US011219520B2

(12) United States Patent
Nash (10) Patent No.: US 11,219,520 B2
(45) Date of Patent: Jan. 11, 2022

(54) SHAPE MEMORY POLYMER FOAMS TO SEAL SPACE AROUND VALVES (71) Applicant: SHAPE MEMORY MEDICAL, INC., Santa Clara, CA (US)

(72) Inventor: Landon D. Nash, Sunnyvale, CA (US)

(73) Assignee: SHAPE MEMORY MEDICAL, INC., Santa Clara, CA (US)

( * ) Notice: Subject to any disclaimer, the term of this patent is extended or adjusted under 35 U.S.C. 154(b) by 290 days.

(21) Appl. No.: 16/487,207

(22) PCT Filed: Mar. 14, 2018

(86) PCT No.: PCT/US2018/022468
§ 371 (c)(1),
(2) Date: Aug. 20, 2019

(87) PCT Pub. No.: WO2018/170149
PCT Pub. Date: Sep. 20, 2018

(65) Prior Publication Data
US 2021/0068947 A1 Mar. 11, 2021

Related U.S. Application Data (60) Provisional application No. 62/471,131, filed on Mar. 14, 2017.

(51) Int. Cl.
A61F 2/24 (2006.01)
A61L 27/04 (2006.01)
A61L 27/06 (2006.01)
A61L 27/18 (2006.01)
A61L 27/26 (2006.01)
(Continued)

(52) U.S. Cl.
CPC .......... *A61F 2/2418* (2013.01); *A61L 27/042* (2013.01); *A61L 27/045* (2013.01); *A61L 27/06* (2013.01); *A61L 27/18* (2013.01); *A61L 27/26* (2013.01); *A61L 27/34* (2013.01); *C08J 9/228* (2013.01); *A61F 2210/0014* (2013.01);
(Continued)

(58) Field of Classification Search
CPC .... A61F 2/2418; A61F 2/2415; A61F 2/2412; A61L 27/042; A61L 27/045
See application file for complete search history.

(56) References Cited

U.S. PATENT DOCUMENTS 4,663,358 A  5/1987  Hyon et al.
4,706,671 A  11/1987  Weinrib
(Continued)

FOREIGN PATENT DOCUMENTS

CN  104758088 A  7/2015
CN  106132352 A  11/2016
(Continued)

OTHER PUBLICATIONS

Japanese Patent Office, Notice of Reason(s) for Rejection dated Dec. 16, 2020 in Japanese patent application No. 2019-550680, 6 pages total.
(Continued)

*Primary Examiner* — Jason-Dennis N Stewart
(74) *Attorney, Agent, or Firm* — Trop, Pruner & Hu, P.C.

(57) ABSTRACT

An embodiment includes individual SMP foams that radially expand and fill gaps around a heart valve that may be improperly seated, in an unusual cross section, or has poor apposition against a calcified lesion. Other embodiments are described herein.

28 Claims, 7 Drawing Sheets (51) Int. Cl.
 *A61L 27/34* (2006.01)
 *C08J 9/228* (2006.01)
(52) U.S. Cl.
 CPC .............. *A61F 2210/0071* (2013.01); *A61F 2250/0039* (2013.01); *C08J 2375/12* (2013.01)

(56) References Cited

U.S. PATENT DOCUMENTS

| | | | |
|---|---|---|---|
| 4,994,069 | A | 2/1991 | Ritchart et al. |
| 5,045,601 | A | 9/1991 | Capelli et al. |
| 5,049,591 | A | 9/1991 | Hayashi et al. |
| 5,192,301 | A | 3/1993 | Kamiya et al. |
| 5,207,709 | A | 5/1993 | Picha |
| 5,330,483 | A | 7/1994 | Heaven et al. |
| 5,354,295 | A | 10/1994 | Guglielmi et al. |
| 5,418,261 | A | 5/1995 | Helsemans et al. |
| 5,429,583 | A | 7/1995 | Paulus et al. |
| 5,456,693 | A | 10/1995 | Conston |
| 5,506,300 | A | 4/1996 | Ward |
| 5,522,836 | A | 7/1996 | Palermo |
| 5,634,936 | A | 6/1997 | Linden et al. |
| 5,674,242 | A | 10/1997 | Phan et al. |
| 5,690,671 | A | 11/1997 | McGurk et al. |
| 5,762,630 | A | 6/1998 | Bley et al. |
| 5,846,247 | A | 12/1998 | Unsworth et al. |
| 5,895,398 | A | 4/1999 | Wensel et al. |
| 5,911,737 | A | 6/1999 | Lee et al. |
| 5,957,966 | A | 9/1999 | Schroeppel et al. |
| 5,964,744 | A | 10/1999 | Balbierz et al. |
| 6,034,149 | A | 3/2000 | Bleys et al. |
| 6,059,815 | A | 5/2000 | Lee et al. |
| 6,086,599 | A | 7/2000 | Lee et al. |
| 6,090,072 | A | 7/2000 | Kratoska et al. |
| 6,102,917 | A | 8/2000 | Maitland et al. |
| 6,156,842 | A | 12/2000 | Hoenig et al. |
| 6,165,193 | A | 12/2000 | Greene et al. |
| 6,238,403 | B1 | 5/2001 | Greene, Jr. et al. |
| 6,293,960 | B1 | 9/2001 | Ken |
| 6,296,622 | B1 | 10/2001 | Kurz et al. |
| 6,458,127 | B1 | 10/2002 | Truckai et al. |
| 6,551,340 | B1 | 4/2003 | Konya et al. |
| 6,583,194 | B2 | 6/2003 | Sendijarevic |
| 6,599,234 | B1 | 7/2003 | Gray et al. |
| 6,599,448 | B1 | 7/2003 | Ehrhard et al. |
| 6,616,617 | B1 | 9/2003 | Ferrera et al. |
| 6,855,153 | B2 | 2/2005 | Saadat |
| 7,308,738 | B2 | 12/2007 | Barvosa-Carter et al. |
| 7,386,203 | B2 | 6/2008 | Maitland et al. |
| 7,422,714 | B1 | 9/2008 | Hood et al. |
| 7,611,524 | B1 | 11/2009 | Maitland et al. |
| 7,744,604 | B2 | 6/2010 | Maitland et al. |
| 7,828,790 | B2 | 11/2010 | Griffin |
| 8,133,256 | B2 | 3/2012 | Wilson et al. |
| 8,343,167 | B2 | 1/2013 | Henson |
| 8,449,592 | B2 | 5/2013 | Wilson et al. |
| 8,449,604 | B2 | 5/2013 | Moaddeb et al. |
| 8,888,675 | B2 | 11/2014 | Stankus et al. |
| 9,018,273 | B2 | 4/2015 | Ito et al. |
| 9,051,411 | B2 | 6/2015 | Wilson et al. |
| 9,119,714 | B2 | 9/2015 | Shandas et al. |
| 10,010,327 | B2 | 7/2018 | Wilson et al. |
| 2002/0010481 | A1 | 6/2002 | Jayaraman |
| 2002/0095169 | A1 | 7/2002 | Maitland et al. |
| 2002/0113066 | A1 | 8/2002 | Stark et al. |
| 2002/0142119 | A1 | 10/2002 | Seward et al. |
| 2002/0165582 | A1 | 11/2002 | Porter |
| 2003/0028209 | A1 | 2/2003 | Teoh et al. |
| 2003/0216804 | A1 | 11/2003 | DeBeer |
| 2003/0236533 | A1 | 12/2003 | Wilson et al. |
| 2004/0030062 | A1 | 2/2004 | Mather et al. |
| 2004/0091543 | A1 | 5/2004 | Bell |
| 2005/0021074 | A1 | 1/2005 | Elliott |
| 2005/0038460 | A1 | 2/2005 | Jayaraman |
| 2005/0043755 | A1 | 2/2005 | Wilson et al. |
| 2005/0075405 | A1 | 4/2005 | Wilson et al. |
| 2005/0085693 | A1 | 4/2005 | Belson et al. |
| 2005/0165480 | A1 | 7/2005 | Jordan et al. |
| 2005/0182428 | A1 | 8/2005 | Bearinger et al. |
| 2005/0192621 | A1 | 9/2005 | Wallace et al. |
| 2005/0228417 | A1 | 10/2005 | Teitelbaum et al. |
| 2005/0267570 | A1 | 12/2005 | Shadduck |
| 2005/0274454 | A1 | 12/2005 | Extrand |
| 2005/0274455 | A1 | 12/2005 | Extrand |
| 2006/0009785 | A1 | 1/2006 | Maitland et al. |
| 2006/0271172 | A1 | 11/2006 | Tehrani |
| 2007/0016233 | A1 | 1/2007 | Ferrera et al. |
| 2007/0104752 | A1 | 5/2007 | Lee et al. |
| 2007/0135907 | A1 | 6/2007 | Wilson et al. |
| 2008/0019657 | A1 | 1/2008 | Maitland et al. |
| 2008/0051829 | A1 | 2/2008 | Eidenschink et al. |
| 2008/0109057 | A1 | 5/2008 | Calabria et al. |
| 2008/0114454 | A1 | 5/2008 | Peterman et al. |
| 2008/0243167 | A1 | 10/2008 | Paganon |
| 2008/0269745 | A1 | 10/2008 | Justin |
| 2009/0054918 | A1 | 2/2009 | Henson |
| 2009/0093674 | A1 | 4/2009 | Adams |
| 2009/0130391 | A1 | 5/2009 | Taya |
| 2009/0248141 | A1 | 10/2009 | Shandas et al. |
| 2009/0264835 | A1 | 11/2009 | Schuermann |
| 2009/0280330 | A1 | 11/2009 | Xie et al. |
| 2011/0015613 | A1 | 1/2011 | Anzai |
| 2012/0158034 | A1 | 6/2012 | Wilson et al. |
| 2013/0089576 | A1 | 4/2013 | Maitland et al. |
| 2013/0253086 | A1 | 9/2013 | Wilson et al. |
| 2013/0317541 | A1 | 11/2013 | Singhal et al. |
| 2014/0142207 | A1 | 5/2014 | Singhal et al. |
| 2014/0277057 | A1 | 9/2014 | Ortega et al. |
| 2014/0277388 | A1 | 9/2014 | Skemp |
| 2014/0277428 | A1 | 9/2014 | Skemp et al. |
| 2015/0119706 | A1 | 4/2015 | Zheng-Rong |
| 2015/0313606 | A1 | 11/2015 | Wilson et al. |
| 2016/0106538 | A1 | 4/2016 | Mitra et al. |

FOREIGN PATENT DOCUMENTS

| | | |
|---|---|---|
| JP | 2006-07023 | 3/2006 |
| KR | 10-2010-0112842 | 10/2010 |
| WO | 2004016205 A2 | 2/2004 |
| WO | 2009013752 A2 | 1/2009 |
| WO | WO2015153755 | 10/2015 |
| WO | WO2016149070 | 9/2016 |

OTHER PUBLICATIONS

Atkinson et al., "Usable Frequencies in Hyperthermia with Thermal Seeds," IEEE Transactions on Biomedical Engineering, vol. BNE-31, No. 1, 1984, pp. 70-75.

Cetas et al., "A Ferrite Core/Metallic Sheath Thermoseed for Interstitial Thermal Therapies," IEEE Transactions on Biomedical Engineering, vol. 45, No. 1, 1998, pp. 68-77.

Hergt et al., "Physical Limits of Hyperthermia Using Magnetite Fine Particles," IEEE Transactions on Magnetics, vol. 34, No. 5, 1998, pp. 3745-3754.

Irie, "Shape Memory Polymers," Ch. 9 from book Shape Memory Materials, Cambridge University Press, UK, 1998, 17 pages.

Jojo et al., "Consideration of Handy Excitation Apparatus for the Inductive Hyperthermia," IEEE Transactions on Magnetics, vol. 37, No. 4, 2001, pp. 2944-2946.

Jordan et al., "Inductive Heating of Ferrimagnetic Particles and Magnetic Fluids: Physical Evaluation and Their Potential for Hyperthermia," Int. J. Hyperthermia, vol. 9, No. 1, 1993, pp. 51-68.

Kimura et al., "VLF Induction Heating for Clinical Hyperthermia," IEEE Transactions on Magnetics, vol. MAG-22. No. 6, 1986, pp. 1897-1900.

Matsuki et al., "High Quality Soft Heating Method Utilizing Temperature Dependence of Permeability and Core Loss of Low Curie Temperature Ferrite," IEEE Transactions on Magnetics, vol. MAG-21, No. 5, 1985, pp. 1927-1929.

McCurrie, "Ferromagnetic Materials Structure and Properties," Academic Press, London, 1994. 4 pages.

(56) References Cited

OTHER PUBLICATIONS

Oleson, "A Review of Magnetic Induction Methods for Hyperthermia Treatment of Cancer," IEEE Transactions on Biomedical Engineering, vol. BME-31, No. 1, 1984, pp. 91-97.
Paulus et al., "Evaluation of Inductively Heated Ferromagnetic Allow Implants for Therapeutic Interstitial Hypertheria," IEEE Transactions on Biomedical Engineering, vol. 43, No. 4, 1996, pp. 406-413.
Sato et al., "An Experimental Study on a Soft Heating Method for Clinical Application of Interstitial Hyperthermia," IEEE Transactions on Magnetics, vol. 29, No. 6, 1993, pp. 3331-3333.
Stauffer et al., "Observations on the Use of Ferromgnetic Implants for Inducing Hyperthermia," IEEE Transactions on Biomedical Engineering, vol. BME-31, No. 1, 1984, pp. 76-90.
Stauffer et al., "Practical Induction Heating Coil Designs for Clinical Hyperthermia with Ferromgnetic Implants," IEEE Transactions on Biomedical Engineering, vol. 41, No. 1, 1994, pp. 17-28.
Wetzel et al., "Feasibility of Magnetic Particle Films for Curie Temperature-Controlled Processing of Composite Materials," Army Research Laboratory, ARL-TR-2431, 2001, 58 pages.
Furopean Patent Office, Extended European Search Report dated Feb. 14, 2019 in European Patent Application No. 16831157.9.
The International Searching Authority, Written Opinion of the International Searching Authority and the International Search Report dated Oct. 13, 2016 in International Application No. PCT/US16/43711, eight pages.
Singhal, et al., "Ultra Low Density and Highly Crosslinked Biocompatible Shape Memory Polyurethane Foams," Journal of Polymer Science Part B: Polymer Physics, Mar. 4, 2012, pp. 724-737, vol. 50, Wiley Periodicals, Inc.
Small, et al., "Biomedical applications of thermally activated shape memory polymers," Journal of Material Chemistry, May 14, 2010, pp. 3356-3366, vol. 20, Issue 18.
Singhal, et al., "Low density biodegradable shape memory polyurethane foams for embolic biomedical applications," Acta Biomateralia, Feb. 28, 2013, 35 pages.
European Patent Office, Extended European Search Report dated Jun. 29, 2015 for European Patent Application No. 11848981.4.
European Patent Office, Communication pursuant to Article 94(3) EPC dated Feb. 27, 2017 for European Patent Application No. 11848981.4.
Ayranci, et al., "Shape Memory Effect of a Thermoset Polymer and its Fiber Reinforced Composites," 18th International Conference on Composite Polymers, pp. 1-5.
Xie, "Recent advances in polymer shape memory," Polymer, Aug. 10, 2011, pp. 4985-5000, vol. 52, Elsevier Ltd.
Behl, et al, "Shape-memory polymers," Materials Today, Apr. 2007, vol. 10, No. 4, pp. 20-28, Elsevier Ltd.
Reddy, et al., "Bioinspired Surfaces with Switchable Adhesion," Advanced Materials, 2007, vol. 19, pp. 3833-3837, Wiley-VCH Verlag GmbH & Co., KGaA, Weinheim.
Hasan, et al., "Effects of Isophorone Diisocyanate on the Thermal and Mechanical Properties of Shape-Memory Polyurethane Foams," Macromolecular Chemistry and Physics, Macromolecular Journals, 2014, pp. 2420-2429, vol. 215, Wiley-VCH Verlag GmbH & Co., KGaA, Weinheim.
European Patent Office, Extended European Search Report dated Mar. 11, 2020 in European patent application No. 17 876 750.5, 7 pages total.
International Searching Authority, "Notification of Transmittal of the International Search Report and the Written Opinion of the International Searching Authority," dated Mar. 19, 2018, in International application No. PCT/US2017/064355.
International Searching Authority, "International Preliminary Report On Patentability," dated Jun. 4, 2019, in International application No. PCT/US2017/064355.
Gaba, R.C., et al., "Embolization of Intracranial Aneurysms With Hydrogel-Coated Coils Versus Inert Platinum Coils Effects on Packing Density, Coil Length and Quantity, Procedure Performance, Cost, Length of Hospital Stay, and Durability of Therapy," Stroke, 2006, pp. 1-8.
O'Hare, A., et al., "HydroCoils, occlusion rates, and outcomes: a large single-center study," American Journal of Neuroradiology, 2010, pp. 1-6.
Maitland, D.J., et al., "Prototype laser-activated shape memory polymer foam device for embolic treatment of aneurysms," J Biomed Opt, 2007. pp. 1-3.
Singhal, P., et al., "Ultra low density and highly crosslinked biocompatible shape memory polyurethane foams," Journal of Polymer Science Part B: Polymer Physics, 2012, pp. 1-27.
Rodriguez, J.N., et al., "In vivo response to an implanted shape memory polyurethane foam in a porcine aneurysm model," Journal of Biomedical 1-23.Materials Research Part A, 2014, pp. 1-23.
Szikora, I., et al., "Histopathologic evaluation of aneurysms treated with Guglielmi detachable coils or matrix detachable microcoils," American journal of neuroradiology, 2006, pp. 1-7.
Boyle, A.J., et al., "In vitro and in vivo evaluation of a shape memory polymer foam-over-wire embolization device delivered in saccular aneurysm models," Journal of Biomedical Materials Research Part B: Applied Biomaterials, 2015, pp. 1-21.
Hwang, W., et al., "Estimation of aneurysm wall stresses created by treatment with a shape memory polymer foam device," Biomech Model Mechanobiol, 2012, pp. 1-34.
Rodriguez, J., et al., "Opacification of Shape Memory Polymer Foam Designed for Treatment of Intracranial Aneurysms," Annals of Biomedical Engineering, 2012, pp. 1-25.
Hasan, S.M., et al., "Modification of shape memory polymer foams using tungsten, aluminum oxide, and silicon dioxide nanoparticles," RSC Advances, 2016, pp. 1-22.
Hasan, S.M., et al., "Tungsten-loaded SMP foam nanocomposites with inherent radiopacity and tunable thermo-mechanical properties," Polymers for Advanced Technologies, 2016, pp. 1-19.
Werner Krause, et al, "Chemistry of X-Ray Contrast Agents, in Contrast Agents II," Topics in Current Chemistry, vol. 222, Springer-Verlag Berlin Heidelberg 2002, 44 pages.
Nirmala R. James, et al., "Polyurethanes With Radiopaque Properties," Jul. 18, 2005, 7 pages.
Landon D. Nash, et al., "Increased X-ray Visualization of Shape Memory Polymer Foams by Chemical Incorporation of Iodine Motifs," Aug. 20, 2017, 16 pages.
Brooks, et al., "Effects of Isophorone Diisocyanate on the Hydrophobicity of Shape memory Polymers," Aug. 9, 2013, 1 page.
International Searching Authority, "Notification of Transmittal of the International Search Report and the Written Opinion of the International Searching Authority," dated Jul. 2, 2018, in International application No. PCT/US2018/022468.
WEBMD, "Aortic Valve Replacement Surgery," Mar. 10, 2017, 8 pages.
Dr. Grzegorz Smolka, et al., "Paravalvular Leak-Important Complication After Implantation Of Prosthetic Valve," vol. 9, No. 8, Nov. 8, 2010, 8 pages.
European Patent Office, Supplementary European Search Report dated Nov. 11, 2020 in European patent application No. 18 768 742.1, 5 pages total.
Chinese Patent Office, First Office Action dated Jan. 6, 2021 in Chinese Patent Application No. 201880017989.3, 14 pages total.

SHAPE MEMORY POLYMER FOAMS TO SEAL SPACE AROUND VALVES

PRIORITY

This application claims priority to U.S. Provisional Patent Application No. 62/471,131 filed on Mar. 14, 2017 and entitled "Shape Memory Polymer Foams to Seal Space Around Valves", the content of which is hereby incorporated by reference.

TECHNICAL FIELD

Embodiments of the invention are in the field of medical devices and, in particular, valves.

BACKGROUND

Surgery to replace a cardiac valve (e.g., aortic or mitral valve) is done for various reasons, such as stenosis or regurgitation of the mitral, aortic, pulmonary, or tricuspid valves. During this surgery, the damaged valve is removed and replaced with an artificial valve. The valve replacement is typically an open-heart surgery. However, a minimally invasive surgery or a catheter procedure to replace the valve may be an option for some people. The artificial valve might be mechanical (made of man-made substances) and/or may be made from animal tissue.

Paravalvular or paraprosthetic leak (PVL) is a complication associated with the implantation of a prosthetic heart valve whether by a traditional (surgical) or a transcatheter (TAVI) approach. Paravalvular or paraprosthetic leak refers to blood flowing through a channel between the structure of the implanted valve and cardiac tissue as a result of a lack of appropriate sealing. The majority of PVL are crescent, oval or roundish-shaped and their track can be parallel, perpendicular or serpiginous. Incidence of PVL, including small non-significant jets, is estimated to be as high as 20%. PVL is also more common with mitral (up to 20%) than aortic prosthetic valves.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Reference will now be made to the drawings wherein like structures may be provided with like suffix reference designations. In order to show the structures of various embodiments more clearly, the drawings included herein are diagrammatic representations. Thus, the actual appearance of the fabricated structures, for example in a photograph, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

Many embodiments addressed herein concern paravalvular leaks. However, embodiments are more generally concerned with leaks associated with implanted valves, whether those valves be cardiac valves, peripheral venous valves, or otherwise.

Applicant determined conventional practices use, for example, PET (Dacron) "skirts" to fill the paravalvular space and promote tissue integration. However, Applicant has further determined such technologies fail to adequately do either of volumetrically filling the paravalvular space or promoting tissue integration. Embodiments described herein utilize shape memory polymer (SMP) foams to fill the space around the valve and promote tissue integration.

For example, an embodiment includes use of a SMP foam incorporated around the annulus of a heart valve to reduce flow around the valve and help integrate the device into the surrounding tissue. More specifically, a SMP foam expands and fills gaps around a valve that may be improperly seated, in an unusual cross section, or has poor apposition against a calcified lesion. For example, the radial expansion of the foam provides volumetric filling around the device. This applies for surgically placed valves, but the shape memory capacity of the foam is particularly useful for endovascular valve delivery.

While many embodiments herein address radial compression of SMP foams (and consequent radial expansion of the SMP foams), other embodiments may employ axial compression/expansion and/or circumferential compression/expansion.

Once implanted, the foam occludes paravalvular leaks and promotes tissue integration for durable occlusion. The porous morphology of the foam encourages acute thrombus formation and device sealing. Over time, this thrombus is replaced with integrated tissue for durable sealing and device incorporation into the surrounding tissue.

An embodiment includes a monolithic foam annulus adhered to a valve. See, for example, the foam annulus in FIG. 4. Adhesion includes weaving valve support struts through the foam (see, e.g., FIG. 1), gluing valve support struts to the foam, and/or coating the valve support struts with a polymer (such as polyurethane) film and adhering the foam to the polymer film. Adhering the foam to the valve support structure ensures it will not dislodge and move downstream to occlude vessels.

Figure 2A:
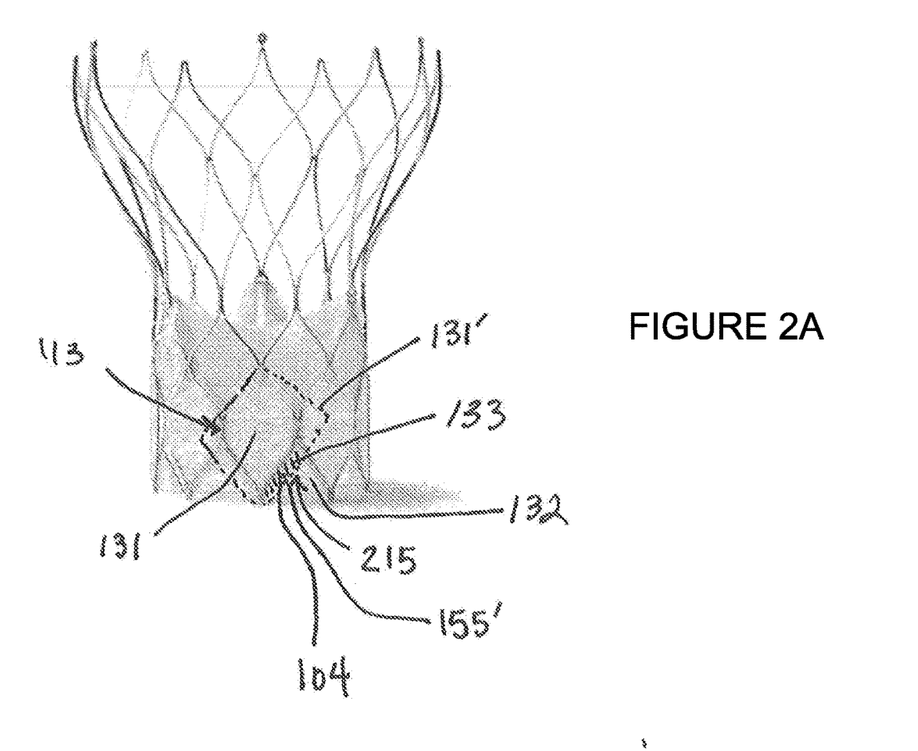
FIG. 2A shows a radially compressed SMP foam in an embodiment.
Figure 2B:
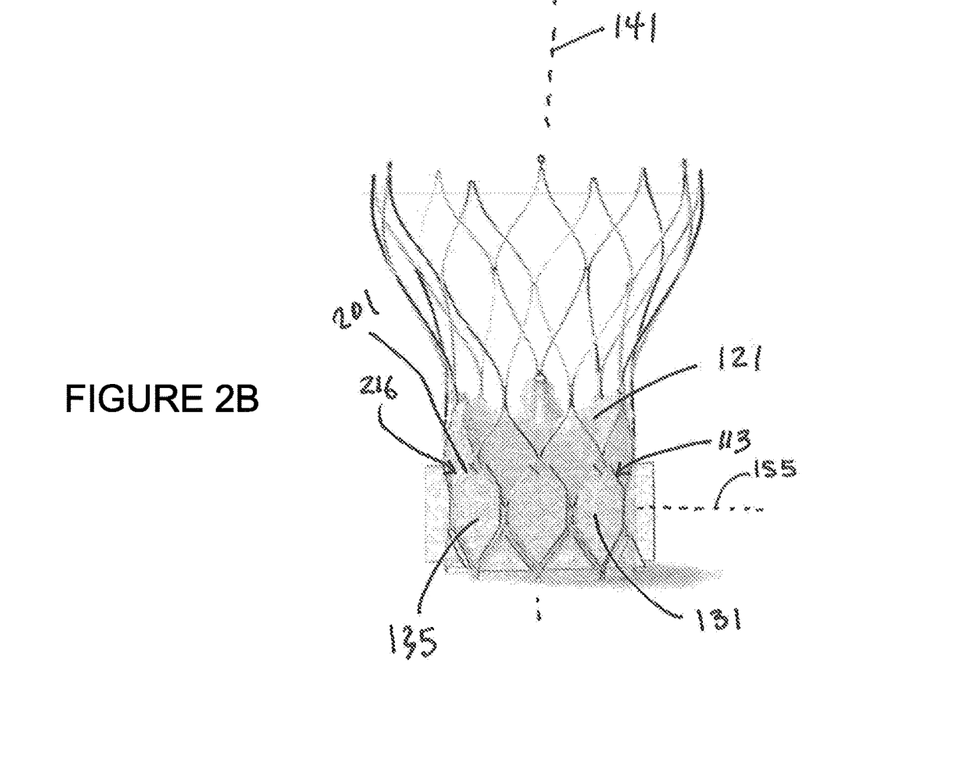
FIG. 2B shows the SMP foam radially expanded.

As seen in FIG. 2B, an embodiment includes independent foam "scales" adhered to the device.

Figure 1:
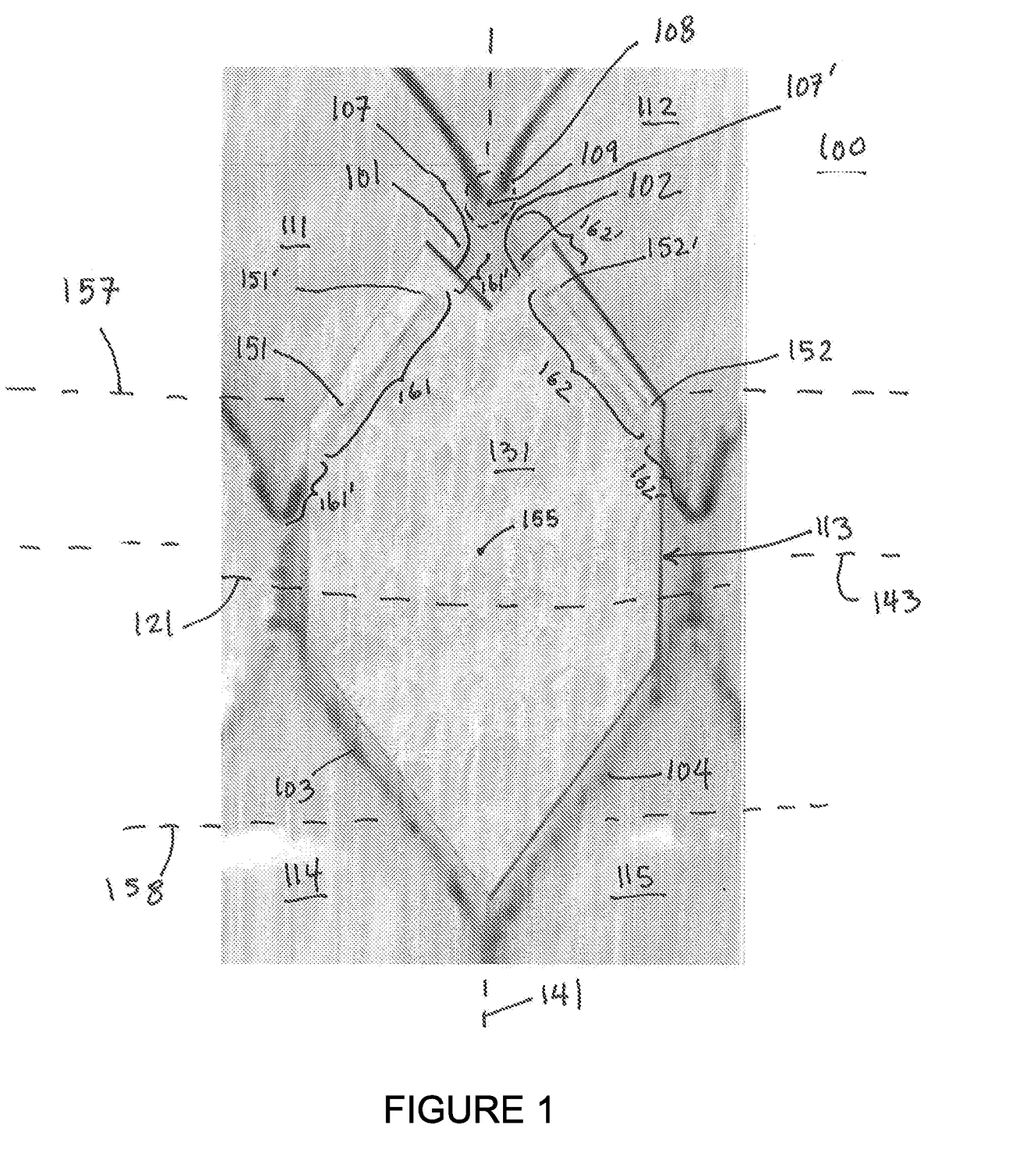
FIG. 1 includes a shape memory polymer (SMP) foam substantially covering a window of a stent in an embodiment.
Figures 3A, 3B:
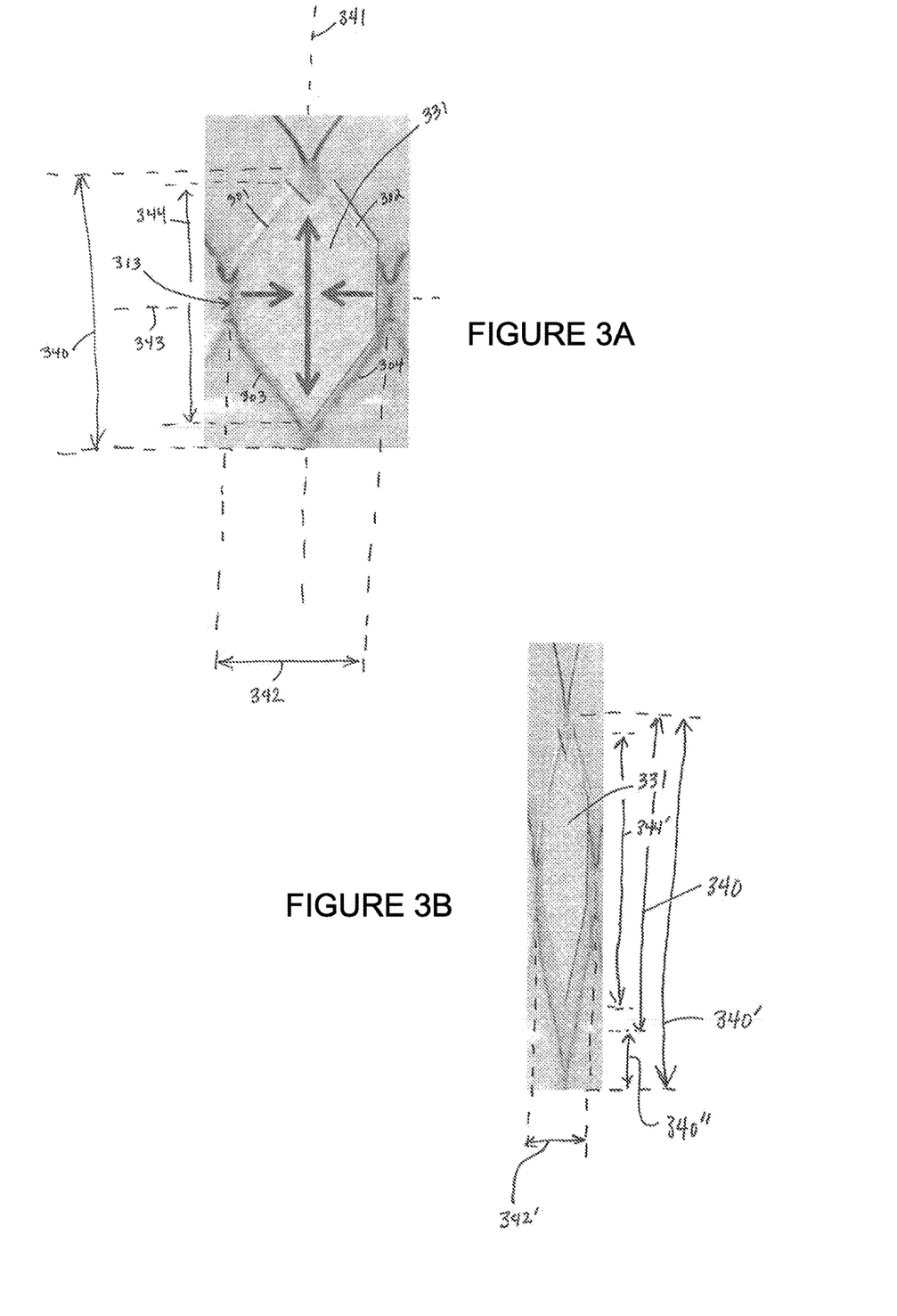
FIG. 3A shows a radially compressed SMP foam in an embodiment.
FIG. 3B shows the radially compressed foam and a stent after the stent is compressed for delivery into a patient.

In an embodiment, Nitinol wire is threaded through polymer foam (see FIGS. 1 and 3A). These wire structures would be threaded through the foam prior to being welded together to form the support structure.

In an embodiment, a bottom of the SMP "scale" is not bound to the Nitinol frame (see FIGS. 1, 3A, and 3B). The foam "scale" embodiment accommodates the anisotropic strain (see, e.g., FIG. 3B) the valve support structure undergoes during radial compression into the delivery catheter. For example, each window of the support structure decreases along the circumferential axis (see, e.g., "horizontal" arrows of FIG. 3A that refer to movement of the Nitinol window), but elongates in the axial direction (see, e.g., "vertical" arrows of FIG. A that refer to movement of the Nitinol window). In other words, the bottom of the scale is free and prevents the foam from undergoing significant tension that could lead to tearing.

In an embodiment, the SMP "scale" includes a window (see upper void in SMP foam of FIG. 1) to accommodate welding or linking neighboring support struts.

Other scales are included in FIGS. 5A, 5B, 6A, 6B, 6C and 7. These foam form factors shown in slides 5A-7 demonstrate different degrees of area filling within each "window" of the support structure. Different foam form factors allow for varying degrees of radial compression and scale folding after compression. Once radially compressed, the flat foam scale may be folded, similar to a catheter balloon, to achieve the minimal crimped cross section that deploys appropriately during delivery.

While many embodiments above address valve sealing, and cardiac valve sealing in particular, other embodiments are not so limited and may include, for example, abdominal aortic aneurysms (AAA) stent graft sealing and the like.

An embodiment includes a foam derived from a reaction between one or more polyols (e.g., HPED and/or TEA) and one or more diisocyanates (e.g., hexamethylene diisocyanate (HDI), trimethyl hexamethylene diisocyanate (TMHDI), and/or isophorone diisocyanate) to form a polyurethane SMP. Embodiments include polyurethane SMP foams synthesized by some combination of: HDI, TMHDI, isophorone diisocyanate, triethanolamine, diethanolamine, butane diol, butyne diol, N,N,N',N' tetrakis (hydroxyl propylene) ethylenediamine.

Other embodiments could include x-ray visible SMP foams. For example, an embodiment includes a foam derived from a reaction between one or more polyols (e.g., 5-Amino-2,4,6-triiodoisophthalic acid; 3-methyl-1,5-pentanediol; 2-butyl-2-ethyl-1,3-propanediol; Hexanetriol; Butanetriol) and one or more diisocyanates (e.g., HDI) to form a polyurethane SMP.

Embodiments provide various means to ensure the foam is protected during device delivery.

In an embodiment the valve is delivered through a large diameter catheter/sheath which allows for a large delivery "ramrod" (that can accommodate significant friction from the expanding device) to deploy the valve from the catheter/sheath. Due to the foam being adhered to the support structure (e.g., foam may be adhered focally to the struts or across the full area of the window) the foam does not shear off during delivery.

With some transcatheter embodiments the foam has a delayed foam expansion. For example, the device may be stored well below body temp and may be programmed (glass transition temperature (Tg) programming) to have a fast expansion time once it achieves body temperature (which may exceed the wet Tg for the foam). The foam may be stored in its moisture plasticized state.

Surgical implantation (as opposed to transcatheter implantation) may have body temperature actuation or higher for the foam.

In some embodiments (e.g., transcatheter or surgical) warm saline is used to expand the foam when ready.

When using foam instead of the conventional Dacron skirt, an embodiment contains the foam in a lubricious sheath (e.g., a sheath made from PTFE) and the surgeon retracts the sheath when she or he is ready to deploy this device. This will minimize the amount of shear force on the foam considering, for example, PTFE is more slippery/has less resistance that most PU catheters.

Embodiments may include low and/or high density foams. In embodiments density is used to balance the mechanical strength of the foam (e.g., higher density reduces shearing/tearing) while minimizing the crimp diameter (e.g., higher density decreases the ability to crimp the foam). An embodiment includes a foam with pore sizes between 50-1500 microns.

Some embodiments ensure the foam does not deploy into the main vessel. For example, the foam is well adhered to support structure and expands radially outward from the lumen. Foam pieces adhered to the valve should not compromise the heart chambers. For example, in an embodiment mechanical constraint is used to prevent the foam from deploying radially inward into the main vessel. For instance, the valve may prevent the inward expansion of the foam. As another example, a polymer membrane located between the foam and the device inner channel may prevent the inward expansion of the foam.

Embodiments may include scales that are not all identical. For example, an embodiment includes multiple rows of scales, some of which include half scales and others of which include full scales. The rows may alternate between two different patterns of scales and/or size of scales.

An embodiment uses both a Dacron skirt and SMP foam. For example, the Dacron skirt acts like a "sheath" of sorts that folds over the crimped foam to help delivery.

Embodiments may be used in different pressure environments (e.g., venous vs. arterial pressure). Such embodiments may employ different pore size/form factors from each other.

Embodiments may also address perivalvular leak for venous valve replacement devices, such as in large veins of the leg.

FIG. 1 includes a system 100 with a stent that includes first, second, third, and fourth struts 101, 102, 103, 104. The stent further includes first, second, third, fourth, and fifth windows 111, 112, 113, 114, 115. Valve 121 is included within the stent (best visible in FIG. 2B). An open-cell polyurethane thermoset SMP foam 131 is configured to expand from a compressed secondary state to an expanded primary state in response to thermal stimulus; and an outer conduit that includes the stent. In FIG. 1 the first and third windows 111, 113 share the first strut 101 and are both immediately adjacent the first strut. The second and third windows 112, 113 share the second strut 102 and are both immediately adjacent the second strut. The fourth and third windows 113, 113 share the third strut 103 and are both immediately adjacent the third strut. The fifth and third windows 115, 113 share the fourth strut 104 and are both immediately adjacent the fourth strut. While struts 101, 103 may be included in a single monolithic length of wire, they constitute separate "struts" as that term is used herein.

In FIG. 1, the SMP foam 131 substantially covers at least 80% of a first face of the third window. This "face" is likely 95% obscured (or more) in the embodiment of FIG. 1. The face is primarily formed by struts 101, 102, 103, 104.

In an embodiment, the first, second, third, and fourth struts each include a shape memory metal, such as Nitinol. However, other embodiments are not so limited and my include stainless steel or other metals. Such non-shape memory metals may be deployed with aid of a balloon or other expansive device. Other embodiments include valves that are surgically implanted.

In FIG. 1, the first and second struts 101, 102 fixedly couple to the SMP foam, and the third and fourth struts 103, 104 do not fixedly couple to the SMP foam. The relevance of this arrangement is expanded upon below. Thus, while foam 131 may touch strut 103 is it not "fixed" to strut 103 and when strut 103 deflects due to lengthening of the stent, foam 131 does not necessarily move with the strut. However, foam 131 is fixed to strut 101 and consequently moves when strut 101 moves. In other words, movement of foam 131 is dependent on strut 101 but not strut 103.

In a first orientation (e.g., when the system is in packaging being shipped to a medical facility), the stent has a first maximum stent outer diameter. As shown in FIG. 3B, window 313 (analogous to window 113 of FIG. 1) has a first window length 340' measured parallel to a long axis 341 of the stent. Also, the window has a first window width 342' measured orthogonal to the long axis of the stent and parallel to a short axis 343 of the stent. The SMP foam 331 is in the compressed secondary state.

In a second orientation the stent has a second maximum stent outer diameter 342 that is greater than the first maximum stent outer diameter 342'. This occurs because to reduce the footprint of the stent (to ready stent for implantation) the stent is compressed (and possibly folded). When doing so the stent may be lengthened along axis 341, which causes necking (narrowed) along axis 343. As a result, window 313 has a second window length 340 that is less than the first window length 340'. Also, window 313 has a second window width 342 that is greater than the first window width 342'. The SMP foam is in the expanded primary state in the second orientation.

In contrast to the changing length of window 313, SMP foam 331 has the same foam length (at least in some embodiments) in the compressed and expanded states. For example, length 344' is substantially (+/−3%) the same as length 344. In some embodiments the foam may have the same width in the compressed and expanded states (although the width appears to change in FIGS. 3A and 3B, in some embodiments the width of the foam does not change). The consistent foam length and width is considered before any folding or pleating of the system occurs. In embodiments the only compression of foam 331 is radial compression (into the page of FIG. 3A), with little or no axial (along axis 341) or circumferential (generally along axis 343) compression/expansion.

Applicant recognized these "crimping dynamics" exist and concern the issue that the metal stent may deform (i.e., axially) to a greater degree than the SMP foam. Further, Applicant recognized that metals such as Nitinol may have a relatively low strain capacity (e.g., 4%) whereas the SMP foam has a relatively high strain capacity. Thus, when the metal stent deforms a great deal axially (along axis 341) that deformation may be greater than any axial deformation of the SMP foam. For example, there may little to no axial deformation of the SMP foam. Thus, a radially compressed SMP foam may not be able to deform to the extent of metal window length differential 340" (340'-340=340"). In various embodiments any axial lengthening of the foam may be 0, 5, 10, 15, or 20% of the axial differential 340".

In response to these crimping dynamics, an embodiment secures foam 331 to some struts of the stent but not to others. For example, in FIG. 1 SMP foam 131 fixedly couples to struts 101, 102 at locations 151, 151' and 152, 152'. Locations 151, 151' and 152, 152' are where struts 101, 102 repeatedly pierce SMT foam 131, thereby securing foam 131 to the stent. In other words, strut 101 pierces the SMP foam 131 in at least one location (e.g., location 151) such that the first strut traverses from a first face of the SMP foam (front face seen in FIG. 1) to a second face of the SMP foam (back face not seen in FIG. 1), the first and second faces opposing each other. Notice the lower half of SMT foam 131 is not fixedly secured to struts 103, 104. In response to the first and second struts 101, 102 fixedly coupling to the SMP foam 131, and the third and fourth struts 103, 104 not fixedly coupling to the SMP foam, the SMP foam is configured to move dependent upon the first and second struts and independent of the third and fourth struts when the apparatus transitions from the first orientation to the second orientation. For example, in FIGS. 3A and 3B foam 331 should "ride" up and down (or slide up and down along axis 341) when struts 301, 302 move up and down along axis 341. However, an extreme deflection downwards by struts 303, 304 should not rip or damage the cells of SMT foam 331 since the foam is largely independent of movements of struts 303, 304.

Regarding the coupling of foam 131 to various struts, the SMT foam may couple to the stent in other ways. For example, in an embodiment an adhesive (e.g., UV epoxy weld that uses Dymax 203A-CTH-F to bind Nitinol strut to polyurethane of the SMP foam) couples the SMP foam 131 to the first and second struts 101, 102. The adhesive may be applied along length 161, 162 but absent from length 161', 162' and further absent from struts 103, 104. The adhesive is not seen in FIG. 1 as it is between foam 131 and the struts. Masking may be used at areas 161', 162', 103, 104 to ensure no adhesive is applied to those areas. The masking (e.g., an oxide or nitride) may then be removed later in the process in some embodiments.

In an embodiment the adhesive includes an un-foamed polyurethane coating directly contacting the first strut 101 and fixedly attached to the first strut. The SMP foam 131 directly contacts the polyurethane coating and fixedly attaches to the polyurethane coating. As a result, the polyurethane coating fixedly attaches the SMP foam 131 to the first strut 101. Thus, for a polyurethane foam the adhesion to another polyurethane provides for a stronger adhesion between the adhesive and the foam. For example, the un-foamed polyurethane coating may include a neat polyurethane.

In an embodiment the polyurethane coating is a cured thermoset. However, in another embodiment the polyurethane coating is a thermoplastic. In an embodiment the polyurethane coating has a chemical composition equal to a chemical composition of the SMP foam. Thus, the adhesion between the foam and adhesive is "like to like" and consequently reliable. For example, both the SMP foam and the adhesive coating may be derived from a reaction between one or more polyols (e.g., HPED and/or TEA) and one or more diisocyanates (e.g., hexamethylene diisocyanate (HDI), trimethyl hexamethylene diisocyanate (TMHDI), and/or isophorone diisocyanate).

In an embodiment, the polyurethane coating is a SMP. That SMP coating may have the same chemical composition of the SMP foam. In an embodiment SMP coating is foamed thereby providing a first foam (inner foam) that couples a second foam (outer foam 131) to the stent strut.

Further regarding the makeup of foam 131, in an embodiment the SMP foam is covalently bonded to iodine to thereby make the foam visible under X-ray imaging (i.e., radiopaque). Again regarding radio-opacity, in an embodiment the SMP foam is a poly(urethane-urea-amide). In an embodiment the iodine is included in a triiodobenzene monomer.

As mentioned above, in the compressed state the foam 131 is compressed radially along a radius 155 that is orthogonal to both the long axis 141 of the stent and the short axis 143 of the stent. This is better seen in FIGS. 2A (compressed) and 2B (expanded radially).

Various embodiments use one or more foam segments in various ways.

For example, in FIG. 1 the SMP foam 131 substantially covers a majority of the face of window 113 but does not cover a majority of any face of any of the first, second, fourth, and fifth windows 111, 112, 114, 115. In the embodiment of FIG. 1, window 113 is immediately adjacent each of the first, second, fourth, and fifth windows 111, 112, 114, 115. No additional stent window is between the window 114 and any of the windows 111, 112, 114, 115.

For example, FIG. 2A discloses SMP foam 131. Further, FIG. 2A includes an additional open-cell polyurethane thermoset SMP foam 132, the additional SMP foam being configured to expand from a compressed secondary state to an expanded primary state in response to thermal stimulus. Foam 132 substantially covers a first face of the fourth window 215, the fourth window having the first face and a second face that oppose one another. At least a portion of fourth strut 104 fixedly couples to the additional SMP foam 132 (but not to foam 131). In the first orientation the additional SMP foam is in the compressed secondary state and in a second orientation the additional SMP foam is in the expanded primary state.

In an embodiment, foam 131 may be slightly enlarged such that foam 131 extends to boundaries 131'. As a result the enlarged SMP foam 131 and the additional SMP foam 132 overlap one another (see area 133 for area of overlap) such that an axis (see dot 155' showing axis going into the page) intersects both the SMP foam 131 and the additional SMP foam 132. Axis 155' is orthogonal to the long axis 141 of the stent and to the short axis 143 of the stent.

As seen in FIG. 2A, SMP foam 131 has a first surface area. Additional foam 132 has a second surface area. The first surface area is at least 20% greater than the second surface area. However, in other embodiments one foam segment may be 30, 40, 50, 60, 70, 80, 90% or more greater in surface area than another foam segment.

In the Embodiment of FIG. 2B, foam 131 exists in conjunction with foam 135. Additional open-cell polyurethane thermoset SMP foam 135 is configured to expand from a compressed secondary state to an expanded primary state in response to thermal stimulus. Additional SMP foam 135 substantially covers a first face of a sixth window 216 included in the stent; the sixth window having the first face and a second face that oppose one another. Additional SMP foam 135 does not substantially cover the third window 113. SMP foam 131 does not substantially cover the sixth window 216. An additional strut 201 fixedly couples to the additional SMP foam 135 (similar to how strut 101 couples to foam 131), the additional strut being included in the sixth window 216. In the first orientation the additional SMP foam 135 is in the compressed secondary state and in a second orientation the additional SMP foam is in the expanded primary state.

Again regarding FIG. 1, a first plane 157, parallel to the short axis 143 of the stent, intersects the SMP foam 131, the first and second struts 101, 102, and the first, second, and third windows 111, 112, 113. A second plane 158, parallel to the short axis of the stent, intersects the SMP foam 131, the third and fourth struts 103, 104, and the third, fourth, and fifth windows 113, 114, 115. The first plane 157 does not intersect either of the third and fourth struts 103, 104. The first plane 157 does not intersect either of the fourth and fifth windows 114, 115. The second plane 158 does not intersect either of the first and second struts 101, 102. The second plane 158 does not intersect either of the first and second windows 111, 112.

In the embodiment of FIG. 1, the first strut 101 couples to the second strut 102 at a first junction 108. An axis 109 (see dot going into the page) intersects the first junction but does not interface the SMP foam 131. The axis 109 is orthogonal to the long axis 141 of the stent and the short axis 143 of the stent. As mentioned above, a strut 101 may be "threaded" through the foam 131 before struts 101, 102 are coupled (e.g., weld) to one another. Therefore a window or void having sidewalls 107, 107' may be formed so the coupling (e.g., weld) can be formed without interference from the already present foam 131.

Regarding the "outer conduit" mentioned above, an embodiment may use a conduit (e.g., tube, sheath, skirt, catheter) to deploy the foam/stent system. In an embodiment the outer conduit includes polytetrafluoroethylene (PTFE), extruded PTFE (ePTFE), or some other relatively low friction material that will put limited shear force on the SMP foam.

Some embodiments may include other conduits in addition or in lieu of the above "outer conduit." For example, an embodiment may include an inner conduit (such as a polyurethane membrane) between the valve and the SMP foam. For instance, a Dacron skirt (or any of various polymer skirts/conduits in various embodiments such as a polyurethane skirt) may be between the valve and stent and may serve to ensure the SMP foam does not expand into main vessel (e.g., aorta). In other embodiments the inner conduit may be between the stent and the SMP foam. An adhesive may couple the foam to the inner conduit. The inner conduit may be coupled to the struts. In such a manner the foam is coupled to the struts via the adhesive and the inner conduit. In one embodiment, a non-foamed SMP adhesive adheres an SMP foam (having the same chemical composition as the adhesive) to a non-shape memory inner conduit (e.g., polyurethane inner conduit), which is coupled to the stent.

Figure 4:
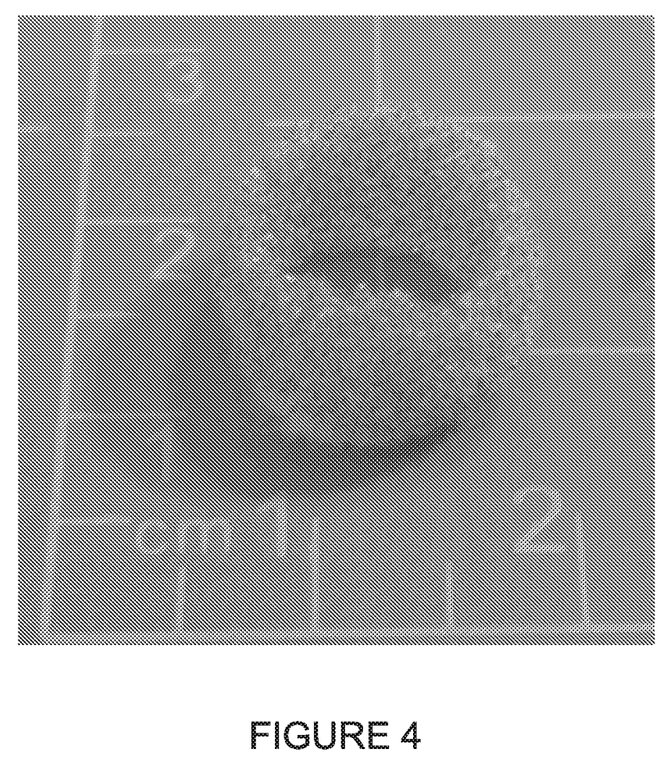
FIG. 4 includes a radio-opaque monolithic SMP foam ring in an embodiment. This also demonstrates the machining capability for the embodiment (i.e., the ability to form the foam into various shapes and sizes).
Figure 5A:
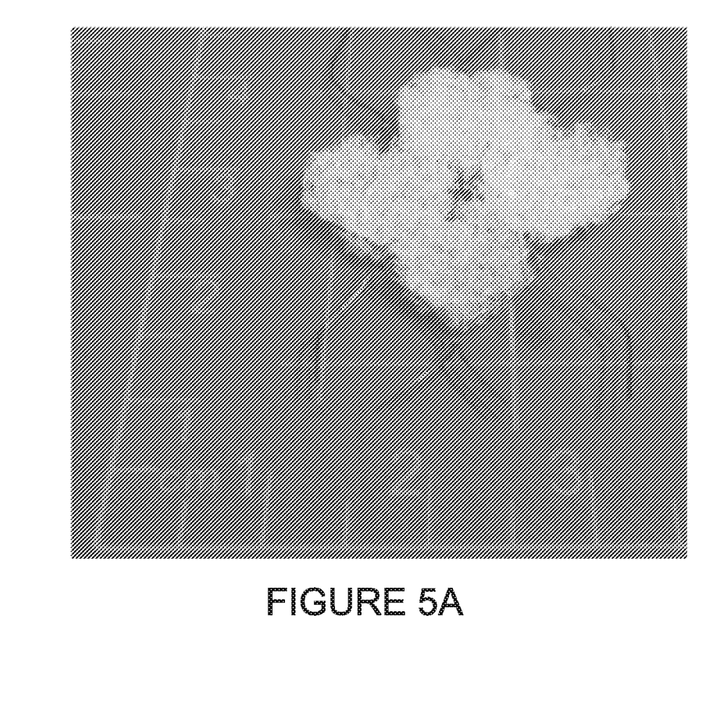
FIG. 5A shows a low density foam matrix in an embodiment.
Figure 5B:
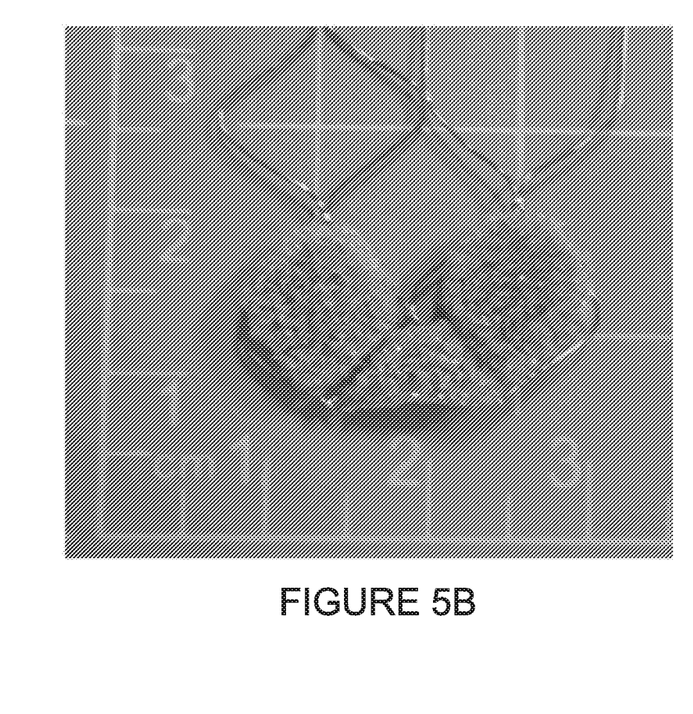
FIG. 5B shows a high density foam that is doped for radio-opacity.
Figure 6A:
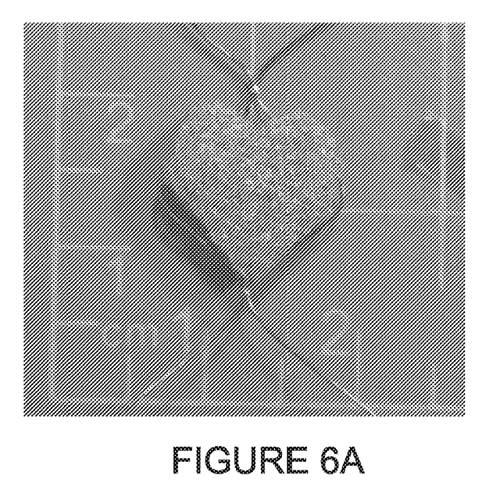
FIG. 6A shows an expanded SMP foam.
Figure 6B:
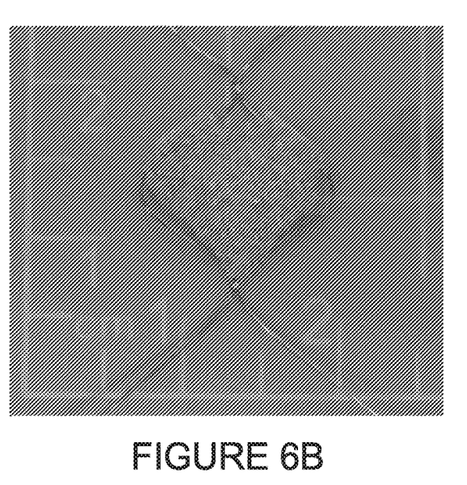
FIGS. 6B and 6C show the SMP foam when crimped/compressed.
Figure 6C:
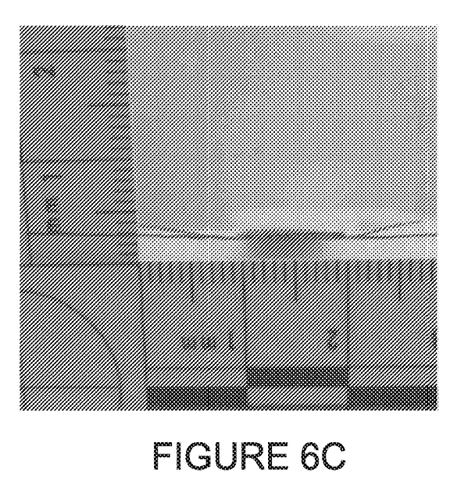
Figure 7:
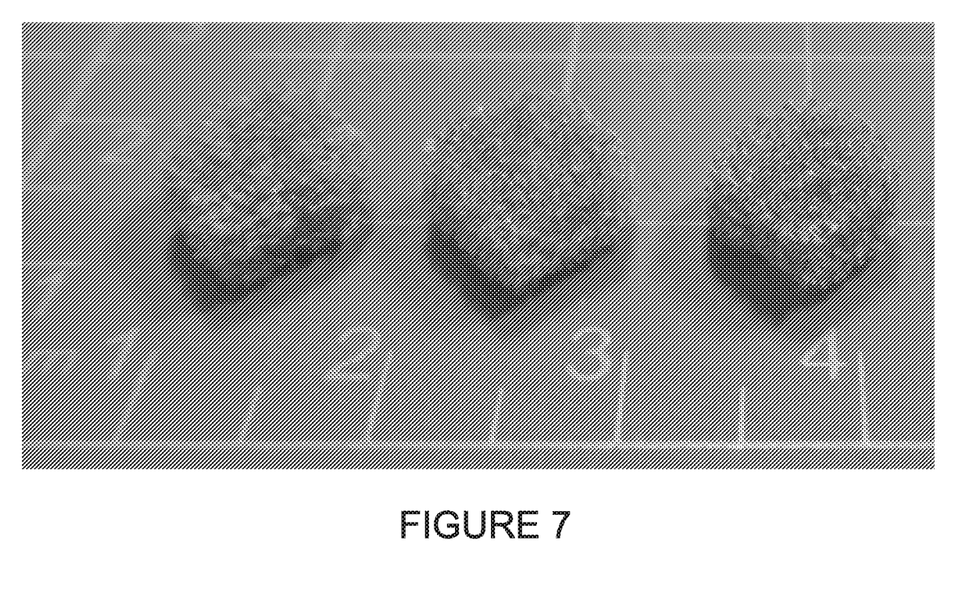
FIG. 7 shows various shapes and sizes that demonstrate the machining capability for embodiments.

As seen in FIG. 4, an embodiment includes a SMP foam that comprises a monolithic SMP foam ring. The SMP foam ring may be outside the stent and surround the stent. The ring may include creases or pleats to help facilitate controlled, repeatable collapsing of the ring when the stent is folded to minimize its profile for implantation. A portion of an upper half of the ring may be fixed to struts while a lower half of the ring may not be fixed to the struts such that the bottom half is not stretched too far when stent is stretched axially. While the embodiment of FIG. 4 is small and suited possibly for a peripheral vessel (e.g., valve for vein) other embodiments may be larger to surround a cardiac valve and the like.

The following examples pertain to further embodiments.

Example 1: An apparatus comprising: a stent that includes (a)(i) first, second, third, and fourth struts, and (a)(ii) first, second, third, fourth, and fifth windows; a valve included within the stent; an open-cell polyurethane thermoset shape memory polymer (SMP) foam, the SMP foam being configured to expand from a compressed secondary state to an expanded primary state in response to thermal stimulus; and an outer conduit that includes the stent; wherein (b)(i) the first and third windows share the first strut and are both immediately adjacent the first strut, (b)(ii) the second and third windows share the second strut are both immediately adjacent the second strut, (b)(iii) the fourth and third windows share the third strut are both immediately adjacent the third strut, and (b)(iv) the fifth and third windows share the fourth strut are both immediately adjacent the fourth strut; wherein the SMP foam substantially covers at least 80% of a first face of the third window, the third window having the first face and a second face that oppose one another; wherein (c)(i) the first and second struts fixedly couple to the SMP foam, and (c)(ii) the third and fourth struts do not fixedly couple to the SMP foam; wherein in a first orientation (d)(i) the stent has a first maximum stent outer diameter, (d)(ii) the third window has a first window length measured parallel to a long axis of the stent, (d)(iii) the third window has a first window width measured orthogonal to the long axis of the stent and parallel to a short axis of the stent, and (d)(iv) the SMP foam is in the compressed secondary state; wherein in a second orientation (e)(i) the stent has a second maximum stent outer diameter that is greater than the first maximum stent outer diameter; (e)(ii) the third window has a second window length that is less than the first window length, (e)(iii) the third window has a second window width that is greater than the first window width, and (e)(iv) the SMP foam is in the expanded primary state; wherein in response to the first and second struts fixedly coupling to the SMP foam, and the third and fourth struts not fixedly coupling to the SMP foam, the SMP foam is configured to move dependent upon the first and second struts and independent of the third and fourth struts when the apparatus transitions from the first orientation to the second orientation.

In other embodiments the SMP foam substantially covers at least 50, 60, 70, 90% of a first face of the third window.

In another version of Example 1: An apparatus comprising: a stent that includes (a)(i) first, second, third, and fourth struts, and (a)(ii) first, second, third, fourth, and fifth windows; a valve included within the stent; an open-cell polyurethane thermoset shape memory polymer (SMP) foam, the SMP foam being configured to expand from a compressed secondary state to an expanded primary state in response to thermal stimulus; and an outer conduit that includes the stent; wherein (b)(i) the first and third windows share the first strut and are both immediately adjacent the first strut, (b)(ii) the second and third windows share the second strut are both immediately adjacent the second strut, (b)(iii) the fourth and third windows share the third strut are both immediately adjacent the third strut, and (b)(iv) the fifth and third windows share the fourth strut are both immediately adjacent the fourth strut; wherein the SMP foam substantially covers at least 80% of a first face of the third window, the third window having the first face and a second face that oppose one another; wherein the first, second, third, and fourth struts each include a shape memory metal; wherein (c)(i) the first and second struts fixedly couple to the SMP foam, and (c)(ii) the third and fourth struts do not fixedly couple to the SMP foam; wherein in a first orientation (d)(i) the stent has a first maximum stent outer diameter, (d)(ii) the third window has a first window length measured parallel to a long axis of the stent, (d)(iii) the third window has a first window width measured orthogonal to the long axis of the stent and parallel to a short axis of the stent, and (d)(iv) the SMP foam is in the compressed secondary state; wherein in a second orientation (e)(i) the stent has a second maximum stent outer diameter that is greater than the first maximum stent outer diameter; (e)(ii) the third window has a second window length that is less than the first window length, (e)(iii) the third window has a second window width that is greater than the first window width, and (e)(iv) the SMP foam is in the expanded primary state; wherein in response to the first and second struts fixedly coupling to the SMP foam, and the third and fourth struts not fixedly coupling to the SMP foam, the SMP foam is configured to move dependent upon the first and second struts and independent of the third and fourth struts when the apparatus transitions from the first orientation to the second orientation.

In another version of Example 1: An apparatus comprising: a stent that includes (a)(i) first, second, third, and fourth struts, and (a)(ii) first, second, third, fourth, and fifth windows; a valve included within the stent; an open-cell polyurethane thermoset shape memory polymer (SMP) foam, the SMP foam having already expanded from a compressed secondary state to an expanded primary state; and an outer conduit that includes the stent; wherein (b)(i) the first and third windows share the first strut and are both immediately adjacent the first strut, (b)(ii) the second and third windows share the second strut and are both immediately adjacent the second strut, (b)(iii) the fourth and third windows share the third strut and are both immediately adjacent the third strut, and (b)(iv) the fifth and third windows share the fourth strut and are both immediately adjacent the fourth strut; wherein the SMP foam substantially covers at least 80% of a first face of the third window, the third window having the first face and a second face that oppose one another; wherein (c)(i) the first and second struts fixedly couple to the SMP foam, and (c)(ii) the third and fourth struts do not fixedly couple to the SMP foam; wherein in a first orientation (d)(i) the stent has a first maximum stent outer diameter, (d)(ii) the third window has a first window length measured parallel to a long axis of the stent, (d)(iii) the third window has a first window width measured orthogonal to the long axis of the stent and parallel to a short axis of the stent; wherein in a second orientation (e)(i) the stent has a second maximum stent outer diameter that is greater than the first maximum stent outer diameter; (e)(ii) the third window has a second window length that is less than the first window length, (e)(iii) the third window has a second window width that is greater than the first window width.

Thus, in some embodiments a product may be shipped with the SMP foam already having been transitioned from its compressed state to a non-compressed state (e.g., already having been plasticized).

Several embodiments discussed herein address windows and struts but embodiments are not limited to any one form of support structure. Metal or polymer support skeletons are viable options that benefit from SMP foams to lessen or prevent a PVL. Further, the SMP foam may have a portion of an upper half of the foam coupled to the support structure while no portion of a bottom half of the SMP foam is coupled to the support structure. This allows for (as an example) lengthening of the support structure without harming a radially compressed SMP foam.

While examples have addressed transitioning a SMP foam to its primary state in response to thermal stimulus, SMP foams may be stimulated based on body temperature, warm saline solution, electromagnetic stimulation via a field supplied external or internal to the body, light from a fiber optic cable, interaction with current supplied via a wire that is in proximity to the foam, and the like.

In some embodiments, a hydrogel may be substituted for the SMP foam.

Example 2: The apparatus of example 1 wherein in the compressed state the first foam is compressed radially along a radius that is orthogonal to both the long axis of the stent and the short axis of the stent.

Example 3: The apparatus of example 2 wherein: the SMP foam has a first foam length in the compressed state, the first foam length being measured parallel to the long axis of the stent; the SMP foam has a second foam length in the expanded state; the first foam length is substantially equal to the second foam length.

Example 4: The apparatus of example 2 wherein the first strut pierces the SMP foam in at least one location such that the first strut traverses from a first face of the SMP foam to a second face of the SMP foam, the first and second faces opposing each other.

Example 5: The apparatus of example 2 wherein: the first strut couples to the second strut at a first junction; an axis intersects the first junction but does not interface the SMP foam; the axis is orthogonal to the long axis of the stent; the axis is orthogonal to the short axis of the stent.

Example 6: The apparatus of example 2 comprising an adhesive that couples the SMP foam to the first and second struts.

Example 7: The apparatus of example 6 wherein: the adhesive includes an un-foamed polyurethane coating directly contacting the first strut and fixedly attached to the first strut; the SMP foam directly contacts the polyurethane coating and fixedly attaches to the polyurethane coating; wherein the polyurethane coating fixedly attaches the SMP foam to the first strut.

Example 8: The apparatus of example 7, wherein the polyurethane coating is a cured thermoset.

Example 9: The apparatus of example 7, wherein the polyurethane coating is a thermoplastic.

Example 10: The apparatus of example 7, wherein the polyurethane coating has a chemical composition equal to a chemical composition of the SMP foam.

Example 11: The apparatus of example 10 wherein the polyurethane coating is a SMP.

Example 12: The apparatus of example 6 comprising an inner conduit between the valve and the SMP foam.

For example, the inner conduit may include a thermoplastic polyurethane membrane deposited over the stent struts. The SMP foam may then be adhered to the membrane with an adhesive. As described herein, the adhesive may include a polyurethane. Thus, an embodiment includes a polyurethane adhesive that adheres a polyurethane SMP foam to a polyurethane membrane (where the membrane adheres to the stent).

Example 13: The apparatus of example 2 wherein the outer conduit includes polytetrafluoroethylene (PTFE).

Example 14: The apparatus of example 2 wherein the SMP foam is covalently bonded to iodine.

Example 15: The apparatus of example 14 wherein the SMP foam is a poly(urethane-urea-amide).

Example 16: The apparatus of example 14 wherein the iodine is included in a triiodobenzene monomer.

Example 17: The apparatus of example 2 wherein the SMP foam is derived from a reaction between one or more polyols and one or more diisocyanates.

Example 18: The apparatus of example 2 wherein: the SMP foam substantially covers a majority of the first face of the third window but does not cover a majority of any face of any of the first, second, fourth, and fifth windows; the third window is immediately adjacent each of the first, second, fourth, and fifth windows; no additional stent window is between the third window and any of the first, second, fourth, and fifth windows.

Example 19: The apparatus of example 2 wherein: an additional open-cell polyurethane thermoset SMP foam, the additional SMP foam being configured to expand from a compressed secondary state to an expanded primary state in response to thermal stimulus; and wherein the additional SMP foam substantially covers a first face of the fourth window, the fourth window having the first face and a second face that oppose one another; wherein the third strut fixedly couples to the additional SMP foam; wherein in the first orientation the additional SMP foam is in the compressed secondary state; wherein in a second orientation the additional SMP foam is in the expanded primary state.

Example 20: The apparatus of example 19 wherein: the SMP foam and the additional SMP foam overlap one another such that an axis intersects both the SMP foam and the additional SMP foam; the axis is orthogonal to the long axis of the stent; the axis is orthogonal to the short axis of the stent.

Example 21: The apparatus of example 2 wherein: an additional open-cell polyurethane thermoset SMP foam, the additional SMP foam being configured to expand from a compressed secondary state to an expanded primary state in response to thermal stimulus; and wherein the additional SMP foam substantially covers a first face of a sixth window included in the stent; the sixth window having the first face and a second face that oppose one another; wherein the additional SMP foam does not substantially cover the third window; wherein the SMP foam does not substantially cover the sixth window; wherein an additional strut fixedly couples to the additional SMP foam, the additional strut being included in the sixth window; wherein in the first orientation the additional SMP foam is in the compressed secondary state; wherein in a second orientation the additional SMP foam is in the expanded primary state.

Example 22: The apparatus of example 21 wherein: the SMP foam has a first surface area; the additional foam has a second surface area; the first surface area is at least 20% greater than the second surface area.

While Example 22 addresses an embodiment with differently sized scales or SMP foam segments, other embodiments may include SMP foam segments of differing density, compression, porosity, and the like. For example, a denser foam may be included directly adjacent a valve annulus while sandwiched axially by less dense foams. This may allow for the greater density foam to withstand elevated forces not present in areas removed from the valve annulus.

Example 23: The apparatus of example 2, wherein: the SMP foam comprises a monolithic SMP foam ring; the SMP foam ring is outside the stent and surrounds the stent.

Example 24: The apparatus of example 2, wherein: a first plane, parallel to the short axis of the stent, intersects the SMP foam, the first and second struts, and the first, second, and third windows; a second plane, parallel to the short axis of the stent, intersects the SMP foam, the third and fourth struts, and the third, fourth, and fifth windows; the first plane does not intersect either of the third and fourth struts; the first plane does not intersect either of the fourth and fifth windows; the second plane does not intersect either of the first and second struts; the second plane does not intersect either of the first and second windows.

Example 25. The apparatus of example 2, wherein the first, second, third, and fourth struts each include at least one of Nitinol, cobalt chromium, and stainless steel.

Example 26: An apparatus comprising: a metal skeleton that includes first, second, third, and fourth struts; a valve included within the skeleton; an open-cell polyurethane thermoset shape memory polymer (SMP) foam, the SMP foam being configured to expand from a compressed secondary state to an expanded primary state in response to thermal stimulus; and wherein (a)(i) the first and second struts fixedly couple to the SMP foam, and (a)(ii) the third and fourth struts do not fixedly couple to the SMP foam; wherein in a first orientation (b)(i) the stent has a first maximum stent outer diameter, (b)(ii) the stent has a first stent length measured parallel to a long axis of the stent, (b)(iii), and the SMP foam is in the compressed secondary state; wherein in a second orientation (c)(i) the stent has a second maximum stent outer diameter that is greater than the first maximum stent outer diameter; (e)(ii) the stent has a second stent length that is less than the first stent length, and (c)(iii) the SMP foam is in the expanded primary state; wherein in response to the first and second struts fixedly coupling to the SMP foam, and the third and fourth struts not fixedly coupling to the SMP foam, the SMP foam is configured to move dependent upon the first and second struts and independent of the third and fourth struts when the apparatus transitions from the first orientation to the second orientation; wherein a first plane, orthogonal to the long axis of the stent, intersects the SMP foam and the first and second struts; wherein a second plane, orthogonal to the long axis of the stent, intersects the SMP foam and the third and fourth struts; wherein the first plane does not intersect either of the third and fourth struts; wherein the second plane does not intersect either of the first and second struts.

Example 1a: An apparatus comprising: a structural support skeleton that includes first, second, third, and fourth struts; a valve included within the skeleton; an open-cell polyurethane thermoset shape memory polymer (SMP) foam, the SMP foam being configured to expand from a compressed secondary state to an expanded primary state in response to thermal stimulus; wherein (a)(i) the first and second struts fixedly couple to the SMP foam, and (a)(ii) the third and fourth struts do not fixedly couple to the SMP foam; wherein in a first orientation (b)(i) the stent has a first maximum stent outer diameter, (b)(ii) the stent has a first stent length measured parallel to a long axis of the stent, (b)(iii), and the SMP foam is in the compressed secondary state; wherein in a second orientation (c)(i) the stent has a second maximum stent outer diameter that is greater than the first maximum stent outer diameter; (e)(ii) the stent has a second stent length that is less than the first stent length, and (c)(iii) the SMP foam is in the expanded primary state; wherein in response to the first and second struts fixedly coupling to the SMP foam, and the third and fourth struts not fixedly coupling to the SMP foam, the SMP foam is configured to move dependent upon the first and second struts and independent of the third and fourth struts when the apparatus transitions from the first orientation to the second orientation; wherein a first plane, orthogonal to the long axis of the stent, intersects the SMP foam and the first and second struts; wherein a second plane, orthogonal to the long axis of the stent, intersects the SMP foam and the third and fourth struts; wherein the first plane does not intersect either of the third and fourth struts; wherein the second plane does not intersect either of the first and second struts.

Thus, not all skeletons must be metal. Some may be formed from polymers and the like.

Example 2a. The apparatus of example 1a wherein: an adhesive directly contacts the first and second struts and SMP foam to directly adhere the SMP foam to each of the first and second struts; neither of the third and fourth struts directly contacts an adhesive that also directly contacts the SMP foam.

Example 3a. The apparatus of example 1a comprising a membrane that contacts the first and second struts, wherein: a location within an upper half of the SMP foam directly adheres to the membrane via an adhesive that directly contacts both the membrane and the SMP foam; a lower half of the SMP foam does not directly adhere to the membrane via any adhesive and is configured to slide over the membrane as the apparatus transitions from the first orientation to the second orientation.

Example 4a: The apparatus according to any one of examples 1a-3a wherein in the compressed state the first foam is compressed radially along a radius that is orthogonal to both the long axis of the stent and the short axis of the stent.

Example 5a: The apparatus of example 4a wherein: the SMP foam has a first foam length in the compressed state, the first foam length being measured parallel to the long axis of the stent; the SMP foam has a second foam length in the expanded state; the first foam length is substantially equal to the second foam length.

Example 6a: The apparatus of example 4a wherein the first strut pierces the SMP foam in at least one location such that the first strut traverses from a first face of the SMP foam to a second face of the SMP foam, the first and second faces opposing each other.

Example 7a: The apparatus of example 4a wherein: the first strut couples to the second strut at a first junction; an axis intersects the first junction but does not interface the SMP foam; the axis is orthogonal to the long axis of the stent; the axis is orthogonal to the short axis of the stent.

Example 8a: The apparatus of example 1a comprising an adhesive that couples the SMP foam to the first and second struts.

Example 9a: The apparatus according to any of examples 2a to 8a wherein: the adhesive includes an un-foamed polyurethane coating directly contacting the first strut and fixedly attached to the first strut; the SMP foam directly contacts the polyurethane coating and fixedly attaches to the polyurethane coating; wherein the polyurethane coating fixedly attaches the SMP foam to the first strut.

Example 10a: The apparatus of example 9a, wherein the polyurethane coating is a cured thermoset.

Example 11a: The apparatus of example 9a, wherein the polyurethane coating is a thermoplastic.

Example 12a: The apparatus of example 9a, wherein the polyurethane coating has a chemical composition equal to a chemical composition of the SMP foam.

Example 13a: The apparatus of example 12a wherein the polyurethane coating is a SMP.

Example 14a: The apparatus of example 4a comprising an inner conduit between the valve and the SMP foam.

For example, the inner conduit may include a thermoplastic polyurethane membrane deposited over the stent struts. The SMP foam may then be adhered to the membrane with an adhesive. As described herein, the adhesive may include a polyurethane. Thus, an embodiment includes a polyurethane adhesive that adheres a polyurethane SMP foam to a polyurethane membrane (where the membrane adheres to the stent).

Example 15a: The apparatus of example 4a wherein the outer conduit includes polytetrafluoroethylene (PTFE).

Example 16a: The apparatus of example 4a wherein the SMP foam is covalently bonded to iodine.

Example 17a: The apparatus of example 16a wherein the SMP foam is a poly(urethane-urea-amide).

Example 18a: The apparatus of example 16a wherein the iodine is included in a triiodobenzene monomer.

Example 19a: The apparatus of example 4a wherein the SMP foam is derived from a reaction between one or more polyols and one or more diisocyanates.

Example 20a: The apparatus of example 4a wherein: the SMP foam substantially covers a majority of the first face of the third window but does not cover a majority of any face of any of the first, second, fourth, and fifth windows; the third window is immediately adjacent each of the first, second, fourth, and fifth windows; no additional stent window is between the third window and any of the first, second, fourth, and fifth windows.

Example 21a: The apparatus of example 4a wherein: an additional open-cell polyurethane thermoset SMP foam, the additional SMP foam being configured to expand from a compressed secondary state to an expanded primary state in response to thermal stimulus; and wherein the additional SMP foam substantially covers a first face of the fourth window, the fourth window having the first face and a second face that oppose one another; wherein the third strut fixedly couples to the additional SMP foam; wherein in the first orientation the additional SMP foam is in the compressed secondary state; wherein in a second orientation the additional SMP foam is in the expanded primary state.

Example 22a: The apparatus of example 21a wherein: the SMP foam and the additional SMP foam overlap one another such that an axis intersects both the SMP foam and the additional SMP foam; the axis is orthogonal to the long axis of the stent; the axis is orthogonal to the short axis of the stent.

Example 23a: The apparatus of example 4a wherein: an additional open-cell polyurethane thermoset SMP foam, the additional SMP foam being configured to expand from a compressed secondary state to an expanded primary state in response to thermal stimulus; and wherein the additional SMP foam substantially covers a first face of a sixth window included in the stent; the sixth window having the first face and a second face that oppose one another; wherein the additional SMP foam does not substantially cover the third window; wherein the SMP foam does not substantially cover the sixth window; wherein an additional strut fixedly couples to the additional SMP foam, the additional strut being included in the sixth window; wherein in the first orientation the additional SMP foam is in the compressed secondary state; wherein in a second orientation the additional SMP foam is in the expanded primary state.

Example 24a: The apparatus of example 23a wherein: the SMP foam has a first surface area; the additional foam has a second surface area; the first surface area is at least 20% greater than the second surface area.

Example 25a: The apparatus of example 4a, wherein: the SMP foam comprises a monolithic SMP foam ring; the SMP foam ring is outside the stent and surrounds the stent.

Example 26a. The apparatus of example 4a, wherein the first, second, third, and fourth struts each include at least one of Nitinol, cobalt chromium, and stainless steel.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a side of a substrate is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first layer "on" a second layer is directly on and in immediate contact with the second layer unless such is specifically stated; there may be a third layer or other structure between the first layer and the second layer on the first layer. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. An apparatus comprising:
   a stent that includes (a)(i) first, second, third, and fourth struts, and (a)(ii) first, second, third, fourth, and fifth windows;
   a valve included within the stent;
   an open-cell polyurethane thermoset shape memory polymer (SMP) foam, the SMP foam being configured to expand from a compressed secondary state to an expanded primary state in response to thermal stimulus; and
   an outer conduit that includes the stent;
   wherein (b)(i) the first and third windows share the first strut and are both immediately adjacent the first strut, (b)(ii) the second and third windows share the second strut and are both immediately adjacent the second strut, (b)(iii) the fourth and third windows share the third strut and are both immediately adjacent the third strut, and (b)(iv) the fifth and third windows share the fourth strut and are both immediately adjacent the fourth strut;
   wherein the SMP foam substantially covers at least 80% of a first face of the third window, the third window having the first face and a second face that oppose one another;
   wherein (c)(i) the first and second struts fixedly couple to the SMP foam, and (c)(ii) the third and fourth struts do not fixedly couple to the SMP foam;
   wherein in a first orientation (d)(i) the stent has a first maximum stent outer diameter, (d)(ii) the third window has a first window length measured parallel to a long axis of the stent, (d)(iii) the third window has a first window width measured orthogonal to the long axis of the stent and parallel to a short axis of the stent, and (d)(iv) the SMP foam is in the compressed secondary state;
   wherein in a second orientation (e)(i) the stent has a second maximum stent outer diameter that is greater than the first maximum stent outer diameter; (e)(ii) the third window has a second window length that is less than the first window length, (e)(iii) the third window has a second window width that is greater than the first window width, and (e)(iv) the SMP foam is in the expanded primary state;

wherein in response to the first and second struts fixedly coupling to the SMP foam, and the third and fourth struts not fixedly coupling to the SMP foam, the SMP foam is configured to move dependent upon the first and second struts and independent of the third and fourth struts when the apparatus transitions from the first orientation to the second orientation.

2. The apparatus of claim 1 wherein in the compressed state the first foam is compressed radially along a radius that is orthogonal to both the long axis of the stent and the short axis of the stent.

3. The apparatus according to claim 2 wherein:
the SMP foam has a first foam length in the compressed state, the first foam length being measured parallel to the long axis of the stent;
the SMP foam has a second foam length in the expanded state;
the first foam length is substantially equal to the second foam length.

4. The apparatus according to claim 2 wherein the first strut pierces the SMP foam in at least one location such that the first strut traverses from a first face of the SMP foam to a second face of the SMP foam, the first and second faces opposing each other.

5. The apparatus according to claim 2 wherein:
the first strut couples to the second strut at a first junction;
an axis intersects the first junction but does not interface the SMP foam;
the axis is orthogonal to the long axis of the stent;
the axis is orthogonal to the short axis of the stent.

6. The apparatus according to claim 2 comprising an adhesive that couples the SMP foam to the first and second struts.

7. The apparatus of claim 6 wherein:
the adhesive includes an un-foamed polyurethane coating directly contacting the first strut and fixedly attached to the first strut;
the SMP foam directly contacts the polyurethane coating and fixedly attaches to the polyurethane coating;
wherein the polyurethane coating fixedly attaches the SMP foam to the first strut.

8. The apparatus of claim 7, wherein the polyurethane coating is a cured thermoset.

9. The apparatus of claim 7, wherein the polyurethane coating is a thermoplastic.

10. The apparatus of claim 7, wherein the polyurethane coating has a chemical composition equal to a chemical composition of the SMP foam.

11. The apparatus according to claim 10 wherein the polyurethane coating is a SMP.

12. The apparatus according to claim 6 comprising an inner conduit between the valve and the SMP foam.

13. The apparatus according to claim 2 wherein the outer conduit includes polytetrafluoroethylene (PTFE).

14. The apparatus according to claim 2 wherein the SMP foam is covalently bonded to iodine.

15. The apparatus of claim 14 wherein the SMP foam is a poly(urethane-urea-amide).

16. The apparatus of claim 14 wherein the iodine is included in a triiodobenzene monomer.

17. The apparatus according to claim 2 wherein the SMP foam is derived from a reaction between one or more polyols and one or more diisocyanates.

18. The apparatus according to claim 2 wherein:
the SMP foam substantially covers a majority of the first face of the third window but does not cover a majority of any face of any of the first, second, fourth, and fifth windows;
the third window is immediately adjacent each of the first, second, fourth, and fifth windows;
no additional stent window is between the third window and any of the first, second, fourth, and fifth windows.

19. The apparatus according to claim 2 wherein:
an additional open-cell polyurethane thermoset SMP foam, the additional SMP foam being configured to expand from a compressed secondary state to an expanded primary state in response to thermal stimulus; and
wherein the additional SMP foam substantially covers a first face of the fourth window, the fourth window having the first face and a second face that oppose one another;
wherein the third strut fixedly couples to the additional SMP foam;
wherein in the first orientation the additional SMP foam is in the compressed secondary state;
wherein in a second orientation the additional SMP foam is in the expanded primary state.

20. The apparatus of claim 19 wherein:
the SMP foam and the additional SMP foam overlap one another such that an axis intersects both the SMP foam and the additional SMP foam;
the axis is orthogonal to the long axis of the stent;
the axis is orthogonal to the short axis of the stent.

21. The apparatus according to claim 2 wherein:
an additional open-cell polyurethane thermoset SMP foam, the additional SMP foam being configured to expand from a compressed secondary state to an expanded primary state in response to thermal stimulus; and
wherein the additional SMP foam substantially covers a first face of a sixth window included in the stent; the sixth window having the first face and a second face that oppose one another;
wherein the additional SMP foam does not substantially cover the third window;
wherein the SMP foam does not substantially cover the sixth window;
wherein an additional strut fixedly couples to the additional SMP foam, the additional strut being included in the sixth window;
wherein in the first orientation the additional SMP foam is in the compressed secondary state;
wherein in a second orientation the additional SMP foam is in the expanded primary state.

22. The apparatus of claim 21 wherein:
the SMP foam has a first surface area;
the additional foam has a second surface area;
the first surface area is at least 20% greater than the second surface area.

23. The apparatus according to claim 2, wherein:
the SMP foam comprises a monolithic SMP foam ring;
the SMP foam ring is outside the stent and surrounds the stent.

24. The apparatus according to claim 2, wherein:
a first plane, parallel to the short axis of the stent, intersects the SMP foam, the first and second struts, and the first, second, and third windows;
a second plane, parallel to the short axis of the stent, intersects the SMP foam, the third and fourth struts, and the third, fourth, and fifth windows;
the first plane does not intersect either of the third and fourth struts;
the first plane does not intersect either of the fourth and fifth windows;
the second plane does not intersect either of the first and second struts;
the second plane does not intersect either of the first and second windows.

25. The apparatus according to claim 2, wherein the first, second, third, and fourth struts each include at least one of Nitinol, cobalt chromium, stainless steel, or combinations thereof.

26. An apparatus comprising:
a metal skeleton that includes first, second, third, and fourth struts;
a valve included within the skeleton;
an open-cell polyurethane thermoset shape memory polymer (SMP) foam, the SMP foam being configured to expand from a compressed secondary state to an expanded primary state in response to thermal stimulus; and
wherein (a)(i) the first and second struts fixedly couple to the SMP foam, and (a)(ii) the third and fourth struts do not fixedly couple to the SMP foam;
wherein in a first orientation (b)(i) the stent has a first maximum stent outer diameter, (b)(ii) the stent has a first stent length measured parallel to a long axis of the stent, (b)(iii), and the SMP foam is in the compressed secondary state;
wherein in a second orientation (c)(i) the stent has a second maximum stent outer diameter that is greater than the first maximum stent outer diameter; (e)(ii) the stent has a second stent length that is less than the first stent length, and (c)(iii) the SMP foam is in the expanded primary state;
wherein in response to the first and second struts fixedly coupling to the SMP foam, and the third and fourth struts not fixedly coupling to the SMP foam, the SMP foam is configured to move dependent upon the first and second struts and independent of the third and fourth struts when the apparatus transitions from the first orientation to the second orientation;
wherein a first plane, orthogonal to the long axis of the stent, intersects the SMP foam and the first and second struts;
wherein a second plane, orthogonal to the long axis of the stent, intersects the SMP foam and the third and fourth struts;
wherein the first plane does not intersect either of the third and fourth struts;
wherein the second plane does not intersect either of the first and second struts.

27. The apparatus of claim 26 wherein:
an adhesive directly contacts the first and second struts and SMP foam to directly adhere the SMP foam to each of the first and second struts;
neither of the third and fourth struts directly contacts an adhesive that also directly contacts the SMP foam.

28. The apparatus of example 26 comprising a membrane that contacts the first and second struts, wherein:
a location within an upper half of the SMP foam directly adheres to the membrane via an adhesive that directly contacts both the membrane and the SMP foam;
a lower half of the SMP foam does not directly adhere to the membrane via any adhesive and is configured to slide over the membrane as the apparatus transitions from the first orientation to the second orientation.

\* \* \* \* \*